United States Patent [19]

Elggren

[11] Patent Number: 4,557,693
[45] Date of Patent: Dec. 10, 1985

[54] HUMAN IDENTIFICATION SYSTEM

[75] Inventor: Richard W. Elggren, Sandy, Utah

[73] Assignee: Exact-1-Dent, Incorporated, Sandy, Utah

[21] Appl. No.: 553,770

[22] Filed: Nov. 18, 1983

[51] Int. Cl.$^4$ .............................................. A61C 5/00
[52] U.S. Cl. ...................................................... 433/229
[58] Field of Search ................. 433/229, 215, 1, 9; 119/3, 51 R; 128/330; 40/300, 301, 302, 303, 304, 2 R; 235/462, 487, 493

[56] References Cited

U.S. PATENT DOCUMENTS

| | | | |
|---|---|---|---|
| Re. 30,594 | 4/1981 | Samis | 433/229 |
| 3,949,233 | 4/1976 | Gluck | 235/462 |
| 3,952,438 | 4/1976 | Propst et al. | 40/300 |
| 4,208,795 | 6/1980 | Muhlemann et al. | 433/226 |
| 4,233,964 | 11/1980 | Jefferts et al. | 128/330 |
| 4,239,261 | 12/1980 | Richardson | 40/2 R |
| 4,433,960 | 2/1984 | Garito et al. | 433/215 |
| 4,512,764 | 4/1985 | Michnick et al. | 433/229 |

OTHER PUBLICATIONS

"ORMCO", Catalog, Torque Edgewise Brackets, p. 15, 5-19-64.

Primary Examiner—Robert Peshock
Attorney, Agent, or Firm—Vaughn W. North; Calvin E. Thorpe; M. Wayne Western

[57] ABSTRACT

A device and method for applying and retaining a unique data carrier to a tooth surface of an individual. The data carrier comprises a thin sheet of material having a data format unique to the individual. This data carrier is attached to the surface of the individual's tooth and is adapted for detection by a reader which can be operated by a third person. All phases of installation and detection of the carrier involve passive, noninvasive techniques which can be applied without regard to age and can be maintained as part of a permanent identification system. The system further comprises a central data bank which becomes a verification source for identifying information carried at the individual's tooth surface.

26 Claims, 6 Drawing Figures

HUMAN IDENTIFICATION SYSTEM

BACKGROUND OF THE INVENTION

2. Field of the Invention

The present invention relates to a method and apparatus for attachment of a data carrier to an individual for the purpose of providing immediate accessibility to information about his medical condition, personal identification, and other pertinent data. More particularly, the present invention pertains to attachment of a data carrier to the individual's anatomy by use of a tooth surface as the attachment medium.

2. Prior Art

The identification of individual human beings has been the focus of attention for hundreds of years. Many different processes and apparatus have been developed for the purpose of improving the accuracy, speed and availability of human identification. The prior art of this field can be substantially divided into two principal categories.

The first category involves those persons who are likely to prefer their identification to remain anonymous. This class includes criminals, persons in hiding, and others who, for various reasons, desire to remain anonymous. Human identification in these circumstances has primarily been the problem of government and private investigative agencies who attempt to obtain an identification based on a piece of clothing, a fingerprint, or some other after-effect of human action.

The second broad classification relating to human identification involves victims of wrongful conduct whose identity is unknown because of death, lack of identification, or numerous other conditions which can necessitate the positive identification of an individual. Such circumstances reach not only deceased or unconscious victims of criminal conduct, but also affect many thousands of persons who are victims of unintentional accidents, amnesia, medical conditions which result in unconsciousness, inability to communicate, or other similar incapacities. This need for human identification is particularly common among children, because of the absence of identification on their person. Therefore, a child may be involved in an accident in a remote neighborhood from the child's home wherein no one is aware of the child's identity.

Often, the need to make a positive identification is extremely urgent. Medical emergencies, for example, frequently require a knowledgeable consent upon the part of parents, guardian, or other individuals entitled to consent to medical treatment. Where an individual carries no identification (such as when jogging, involved in athletic events) or where identification was too cumbersome to be concerned with, identification is extremely difficult and frequently requires many man hours to identify a relative or appropriate party. Even where some identification is on a child's person, the frequent occurrence of split families results in extremely difficult name identification through a telephone book or other community information source.

Despite the long existence of this problem, no adequate solution has yet developed. Police offices and other investigative agencies have full-time staff personnel who become experts in human identification and in all aspects of the broad range of problems associated with re-tracing the prior history or steps of an anonymous individual to identify relatives or other persons of interest. Unfortunately, the success of such identifications leaves substantial room for improvement.

Statistics which are generally believed to reflect only a portion of the total actual missing persons are becoming increasingly alarming. Over 1.5 million children are reported missing for some duration of time in the United States each year. This does not account for those who do not have a report filed as to their missing status. Some 20,000 to 50,000 children disappear each year and their cases remain unsolved, some forever. At least 1,000 missing children cases whose facts suggest foul play remain unresolved each year. In addition, 8,000 children are murdered by strangers each year, with at least 2,000 victims remaining unidentified. The seriousness of these problems has now reached the U.S. Department of Justice where formal studies have commenced to more accurately define the problem areas. Other private and governmental agencies at various levels have likewise been considering the problems of human identification for many years.

Typical methods being applied in the identification process have essentially remained unchanged for many years. Fingerprint and dental analysis remain the primary tools of human identification by law enforcement personnel and medical examiners. In each instance, however, a record must exist for the fingerprint or dental study. Since this record is usually separated from the individual, the ability of human identification by starting with a lost or unconscious person is extremely difficult.

Furthermore, the dominant tool of fingerprinting primarily focuses on individuals having a criminal record, who fall in the classification of those not desiring human identification. As a consequence, the victim frequently does not have a fingerprint record to form the basis of a search. Also, fingerprints are subject to deterioration or damage where an accident involves fire or catastrophic injury. One hundred and thirty years of fingerprinting experience has failed to develop significant improvements, beyond computer search programs which are primarily directed toward those having a criminal history.

Other circumstances calling for human identification arise in emergencies such as accidents or serious illness where the victim is rendered incapacitated. These situations not only require name identification, but may also involve the need to identify a patient's blood type, allergic reactions, prior medical conditions, or other vital medical information. For example, diabetics, epileptics, narcoleptics, heart patients, dialysis patients, and numerous other categories of special health conditions may develop symptoms which are a direct result of the medical condition; however, would not be known as such without some form of medical alert tag. For example, it is estimated that there are approximately 48,000,000 people in the United States who have special medical conditions which require special treatment in emergencies. In addition to the added expense associated with running diagnostic tests to identify these conditions, their occurrence increase the risk of death where immediate treatment cannot be rendered until diagnostic testing is completed. As a consequence, the prior art discloses the use of cards, armbands, and other information sources which are designed to give immediate notice of these unique medical conditions. In each instance, however, the individual must make the effort to maintain this information in a pocket or on his person. Typically, such bracelets or cards are not convenient for wear during jogging, sports events, and numerous other types of activities. Accordingly, a substantial portion of the population of the United States is currently in need of some form of identification means which is retained on the individual, is not subject to destruction, loss, forgetfulness, or any of the numerous other problems which frustrate the realization of human identification, with its related subcategories of information regarding relatives, medical conditions, and other critical data.

OBJECTS AND SUMMARY OF THE INVENTION

It is, therefore, an object of the subject invention to provide a method and apparatus to enable human identification without regard to the individual's state of consciousness, wherein the method and technique involve non-invasive, passive procedures which can be applied to any age group.

It is a further object of this invention to provide identification means for attachment to the anatomy of an individual which will continue with the individual, regardless of circumstance or condition of health.

A further object of the present invention is to incorporate a data format which includes emergency information which can be accessed by third parties for use in critical situations, without regard to the state of consciousness of the individual.

A still further object of the present invention is to provide a readily accessible information source attached directly to the individual which identifies critical medical conditions requiring special treatment in emergencies.

It is a specific object of this invention to provide an identification apparatus and method uniquely adapted for children.

A still further object of the present invention includes the development of a method and apparatus to provide ready access into a master data bank which contains current information on a given individual.

Yet another object of this invention is to provide means and method for direct access to a patient's medical history by way of a data carrier attached to the person's anatomy and accessible by non-invasive means during both emergency and normal conditions.

These and other objects are realized in a human identification system for living bodies including a device and method for applying and retaining a data carrier to an individual wherein all phases of installation and detection of the data carrier involve passive, non-invasive techniques, which are applied with respect to a tooth surface. The inventive method comprises the steps of (i) selecting a carrier material, (ii) adapting the carrier material into a data carrier with a data format and structure designed for attachment at the tooth surface, and (iii) attaching the wafer at the tooth surface without causing damage to tooth enamel or other permanent tooth structure. The data carrier comprises a thin, flexible wafer less than 10 mills in thickness and with dimensional property which enable attachment of all parts of the wafer to a single tooth surface, which includes a personal data format containing information relevant to the individual. The data carrier is used as part of an identification system which further includes a detector capable of identifying the information on the individual for comparison with a reference source which also contains the same identifying information. The system not only enables identification of the individual, but also permits the individual to establish a data bank which can be accessed by the information contained on his tooth surface.

Other objects and benefits of the subject invention will be apparent to those skilled in the art, based on the detailed description that follows.

DETAILED DESCRIPTION OF THE INVENTION

Referring Now to the Figures:

The apparatus and methodology of the subject invention involve the proper preparation, placement and use of a unique data carrier 10 on a tooth surface of an individual for the purpose of providing immediate accessibility to information about his medical condition, personal identification and other pertinent data. Such information might be immediately required, for example, to provide proper treatment or attention in emergencies. The carrier literally becomes part of the individual's anatomy and is not subject to being misplaced, forgotten or separately damaged. Nevertheless, no invasive techniques are required for its emplacement. Furthermore, the carrier requires no conscious effort or attention to maintain its effectiveness.

Figure 1:
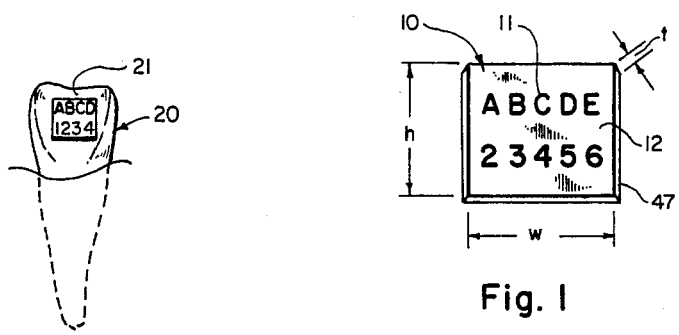
FIG. 1 discloses one embodiment of a data carrier constructed in accordance with the method of the patent invention.
Figure 2:
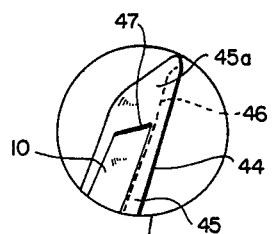
FIG. 2 shows an isolated central incision tooth having been modified with the data carrier in accordance with the present invention.
Figure 3:
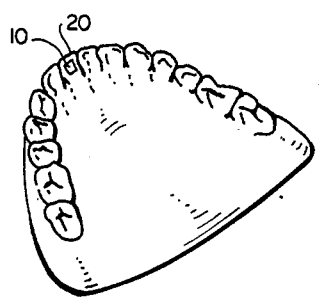
FIG. 3 illustrates an alternative exemplary position for the data carrier shown in FIGS. 1 and 2.

An example of such a data carrier 10 is shown in FIG. 1 and comprises a thin, flexible material 12 having a composition compatible with the oral environment into which the carrier will be placed. The dimensions of the carrier are sufficiently small to enable its attachment to a single tooth 20 as shown in FIGS. 2 and 3. This attachment is at the surface 21 of the tooth 20, requiring no invasive techniques which might damage the tooth structure.

In the preferred embodiment, a plastic composition is used to form the sheet or chip comprising the carrier 10. This material may be photographic film, mylar, kapton or a similar composition which can be coated or modified with a data format 11 formed of aluminum, photographic oxide or other detectable substance consistent with use within the individual's mouth. It should be chemically compatible with bonding agents discussed hereafter, or with other means for attachment to the surface of the tooth.

The dimensions of the carrier should preserve existing comfort and space conditions in the mouth of the individual when in place. It should be thin to avoid the discomfort of having a projecting object permanently attached to the tooth. Although the drawings illustrate a thickness "t" which appears to be substantial, there is no functional value attributable to thickness. Indeed, since the only function of the carrier material is to provide a base for fixation of a data format, a thin film of material would be adequate. It is therefore to be understood that the carrier 10 is to be made as thin as possible, subject to emplacement requirements of the data format and actual positioning of the carrier on the tooth surface. Certainly, it should not be necessary to have greater than 3 to 10 mils.

The remaining width (w) and height (h) dimensions shown in FIG. 1 are restricted to lengths which enable emplacement of the carrier on a single tooth surface. It will therefore be apparent that tooth selection will affect the value of these parameters. Choice of a large molar tooth will allow greater surface area for data format. Smaller teeth will be more restricting. It is unlikely that chip dimensions would ever exceed 3×3 mm. Although the figures show rectangular or square shapes for the wafer, it will be apparent that other shapes would serve just as well. Therefore, it should be understood that any reference to dimensions by height and width could be readily correlated to other shapes of equivalent surface areas.

The tooth 20 illustrated in the figures is a central incisor. Alternatively, the selective tooth might be a mandibular cuspid or molar. The data carrier or wafer 10 is approximately 2.5×2.0 mm in width and height, respectively. It is fabricated of photographic film which has the data format 11 applied by standard photographic techniques. The film is processed and trimmed to the proper size for the particular individual receiving it. It will be apparent that this procedure is well-adapted for large-scale production at minimal expense.

The data format 11 may consist of any information embodied in any form which is incorporated into the data carrier Therefore, this would include electromagnetic signal placed on magnetic tape, photographic imprint, vacuum or chemically deposited data, etched information or other comparable forms of information storage. The selection of the type of data format will depend largely upon the nature of detection system to be applied.

It will be apparent to those skilled in the art that a major factor in selecting a detection system will be the environment in which the system is to operate. For example, use within a hospital is likely to be different than that used as part of a security check required for entrance into a classified area. Likewise, projected use with children for identification purposes suggests a different detection system than that designed for military personnel in combat. It is significant, therefore, that the data carrier set forth in the present invention is capable of being adapted to many applications and forms.

Figure 4:
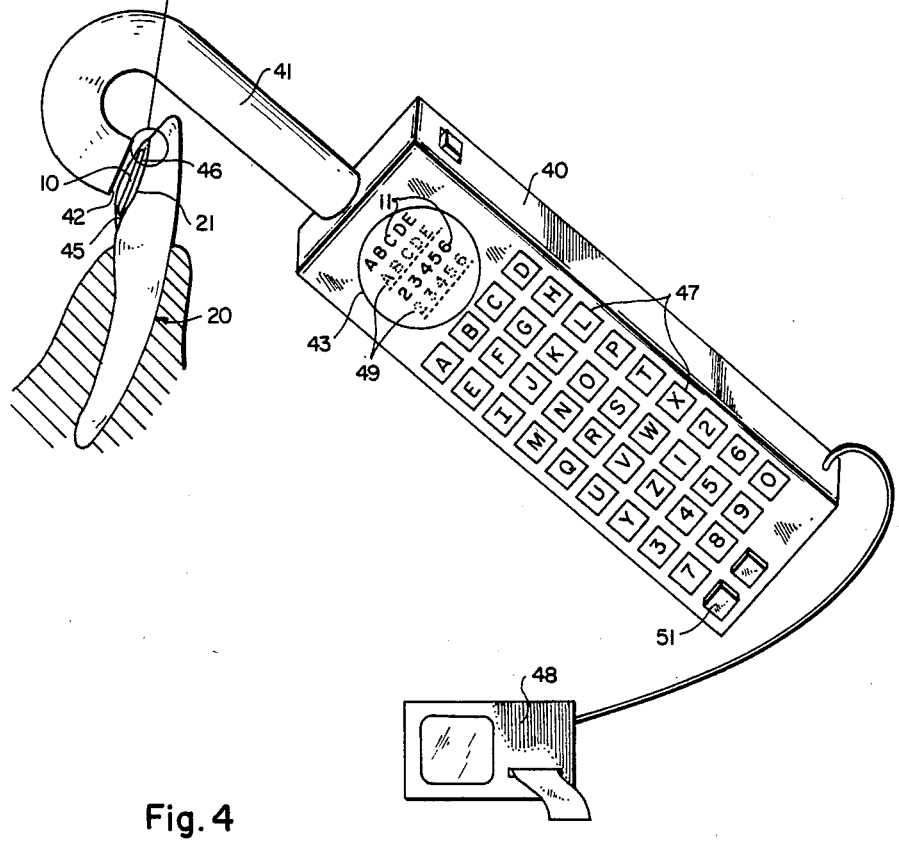
FIG. 4 illustrates the method and apparatus used in connection with the subject invention for attachment and detection of a data carrier on a human tooth.

The data format 11 illustrated in FIG. 2 comprises an alpha-numeric, coded format which enables incorporation of a substantial amount of information on the small area of the chip. With this format, visual detection is possible, such as is illustrated in FIG. 4. The detector or probe 40 in this embodiment comprises a fiber optic wave guide 41 which is curved to access the inside surface 21 of the tooth 20. The end of the probe is polished to provide clear transfer of the data format imaged on the carrier. This image is reflected to a window 43 to enable direct readout of the carrier data. The encasement 45 for the window could likewise contain an input keyboard 47 for typing in the coded information as read on the window. The window 43 includes confirmation print-out 49 to verify the accuracy of manually typed information. This input could then be transmitted to a small computer 48 for processing of the coded information. It is apparent that other embodiments of equivalent design could be developed. For example, the computer could be housed in the detector 40, to comprise a single item of equipment.

Obviously, it is necessary to provide the detector with illumination if direct readout is attempted. This is particularly true where the data carrier is positioned on the inside surface of the tooth. Illumination can be accomplished by encasing a light source in the body of the detector. In this case, the probe provides the wave guide for the light source, as well as the conduit, for return of the image to the window 43.

Figure 5:
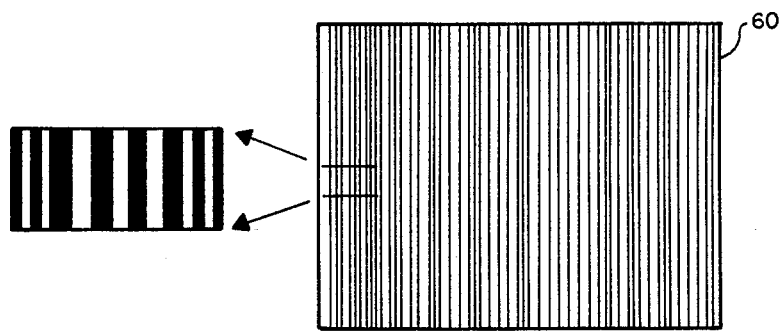
FIG. 5 illustrates a second embodiment for a data format in accordance with the subject invention.

It will be apparent to those skilled in the art that other coded formats may be selected for the data carrier. FIG. 5 illustrates the use of a standard frequency-shift-keying (FSK) or Manchester code 60. This code is easy to implement and requires minimum space for the encoded data. Such a data format could, for example, identify more than one trillion separate individuals by embodying 40 data bits within its format.

Figure 6:
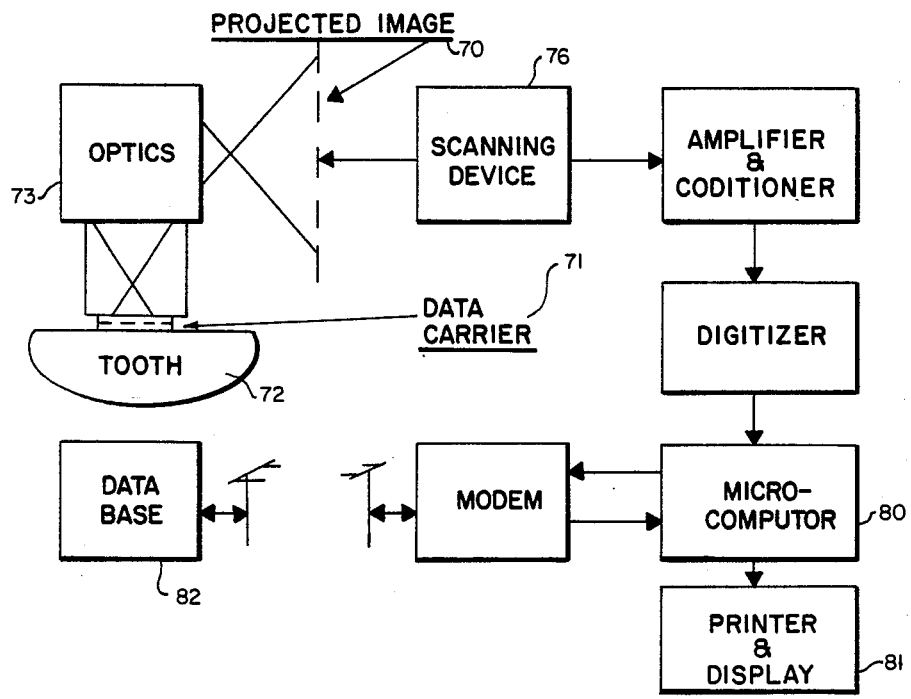
FIG. 6 depicts a block diagram illustrating the method of detection and use applied in accordance with the present invention.

Referring to FIG. 6, the FSK code can be scanned by projection of the data format image 70 from the data carrier 71 which is positioned on the tooth 72. This image is optically transmitted 73 in accordance with well-known imaging techniques to a photodiode array 76 or other acceptable scanning device for electronic conversion of the image to data input for relay to a computer 80. This information can then be printed and displayed, and/or communicated to a primary data base 82 for accessing additional information pertaining to the individual. Such additional information might include a full medical history, names and addresses of relatives, business or military status, or any index of information considered pertinent. This could likewise be printed and/or displayed with the original accessing data format. Further explanation of the intercommunication with a primary data base is considered unnecessary, being well within the state of the art.

In addition to a coded format, the data might be incorporated in uncoded form. This would then permit direct readout by the detector 40 of FIG. 4. Such a format might be suitable where only limited information is desired, or where strong magnification was available in the detector. The choice of coded versus uncoded, or a combination of each, will depend upon the field of use and sophistication desired for the system.

The overall process of selecting a data format and incorporating it into the data carrier falls within the general procedural step of modifying the carrier material to include a singularly unique surface configuration capable of detection as a unique identification of the individual. The various examples of this step have been provided for illustration and are not to be considered limiting. The only condition to be satisfied is that the information be capable of being retrieved by noninvasive, passive detection means such as previously described.

The term "noninvasive" means that no entry into the tooth structure or other part of the body is necessary. In other words, there is no requirement to open a filled cavity or probe the interior of the tooth with x-rays. The data format is exposed to view at the surface of the tooth. The term "passive" has reference to the state of the individual wearing the data carrier. The device is passive in that there is no action required on the part of the individual to obtain a reading. The fact that an individual may be comatose or even deceased would not affect the ability of a third party to access the data carrier and contained information if such access is to be permitted.

The realization and discovery that the data carrier can be attached directly to the surface of the tooth is a significant feature of the present invention. Whereas prior art usage of the tooth structure in connection with identification tags has involved invasive and often painful techniques of drilling into the enamel, the present invention offers no such disadvantage. Rather than frightening children and adults, the attachment procedures required for the instant data carrier are simple, quick and without any significant discomfort. Since all phases of installation and detection of the carrier involve passive, noninvasive techniques which are applied only with respect to the surface of the tooth structure, there need be no use of needles, drills or other equipment which tends to alarm the patient.

Typically, the application of the data carrier will occur in a dental office, and might easily be accomplished in connection with a normal patient visit. Referring to FIG. 4, the area of the tooth surface 21 to carry the data chip 10 is first isolated with cotton rolls and cleaned to expose the enamel rods. This may be accomplished by conventional acid etch techniques involving swabbing a 50% solution amount of phosphoric acid or other suitable acid over the tooth surface. The area is then washed and dried. The purpose of exposing the enamel rods is to provide a rough surface 44 which will enable a strong mechanical bond with bonding material 45 which acts as a substrate to which the carrier is permanently attached.

The bonding material 45 may be a blended methacrylate copolymer or any other conventional polymer which can be applied in liquid form and then hardened in situ. Examples include the aromatic dimethacrylate resin BIS-GMA (bis-glycol-methacrylate), as well as cyanoacrylate systems. Further discussion can be found in Robert G. Craig, *Dental Materials*, pp. 1–51 (1978). This liquid is applied to the tooth surface 44 and flows into the enamel rod structure, providing a bonding surface 46 (shown in phantom lines) which has a strong mechanical bond upon catalysis by uv radiation or other techniques.

Ideally, the selected bonding material is chemically compatible with the carrier composition to provide a chemical bond therebetween. Without such compatibility, greater care must be exercised in developing a strong mechanical bond between the polymer and data chip. This can be done by bevelling the edges 47 of the chip or by using numerous other well-known techniques for securing a mechanical bond.

With the bonding surface 46 now in place and prior to hardening of the polymer, the modified or prepared data carrier 10 is placed on the tooth surface. As previously indicated, the preliminary preparations have involved the dimensional sizing of the chip, as well as the incorporation of an appropriate data format therein. The data carrier 10 is properly positioned and a second coat of clear polymer 45a is placed over the carrier and substrate 46. Ordinarily, this clear polymer would be the same composition as the bonding material 45 or first polymer to ensure optimum bonding between the respective layers 45 and 45a. This operates to seal or encapsulate the data carrier within the protective polymer, with the combination being securely bonded to the enamel tooth surface. Although encapsulation is not essential, it is preferred to create a permanent structure which can withstand the abrasion of eating hard foods, brushing teeth, etc.

With the data carrier properly sealed at the surface of the tooth, on the protected lingual side, the data format should be secure for many years, yet readily available for immediate access in case of emergency or other conditions requiring use. A variety of such uses have been previously alluded to and will now be discussed in greater detail as part of separate methods or processes to which the basic data carrier process and apparatus can be applied.

At the core of functionality is the basic operation of identification. The subject data carrier, for the first time, enables an individual to establish a personal information source which becomes part of his permanent anatomy in a readily accessible form. A child, for example, could be protected from the unpredictable consequences of accident, loss, kidnapping, etc. by use of the subject data carrier which provides the child's name and pertinent information regarding health and persons to contact. This is particularly critical because children are not likely to have a drivers license or other reliable form of identification on their person. If the child is injured and unconscious when away from friends or family, the community is helpless to adequately deal with special needs. Therefore, the present invention provides an excellent method for identification and protection of minors. When the inventive method is expanded to include a central data bank, parents could receive immediate notification of the whereabouts and condition of a lost child, regardless of the child's state of consciousness, by maintaining updated information therein. Where a child is found having the subject data carrier, a local dentist or police officer could quickly initiate the process of identification with the use of a portable detector.

The subject invention is uniquely adapted for use with children and adults having special medical conditions which require immediate or individualized assistance in medical emergencies. A diabetic, hemophiliac, dialysis patient, epileptic, narcoleptic, heart patient or cancer patient requires a unique treatment profile which is only apparent if the special condition is immediately brought to the attention of the attending physician. Because emergency notification cards are not always carried on the person, use of the data carrier can ensure that this critical emergency information is available, regardless of the circumstances.

Because of the large storage capacity of the carrier, many of these conditions can be specifically identified. Unique codes can be assigned to each condition so that a paramedic could access the data carrier by use of a portable detector 40 and be immediately informed of a condition upon detection of that unique code in the data format. Obviously, this would avoid multiple tests presently required to eliminate the numerous conditions which might possibly give rise to the patient's symptoms. The time saved could be the difference between life and death.

The subject data carrier can also be the ready reference for drug allergies of a patient. By scanning the data carrier, a physician could quickly eliminate dangerous medications and apply treatment in accordance with the individual profile of the patient. This profile could be enlarged and constantly updated if linked with a primary data base which would receive input from the patient's ongoing medical history.

A fundamental feature of the present invention is the ability of the data carrier to operate as the access key into the primary data bank previously referenced. The data format could have a coded or uncoded address for the individual data bank entry. The actual contents of the data bank could be controlled by the individual, to thereby prevent breach of privacy. Upon satisfaction of preset conditions (determined by the individual) the data file could be opened via access through the data carrier. The individual would then have the advantage of ensuring that current information was available to key persons on a timely basis.

This method of data access, for example, could be adapted for individual medical histories. Upon acquiring a data carrier, an individual could arrange to have a personal file opened in a central data base established for the purpose. Participating doctors would communicate the individual's medical history to the data base, and would provide updates at each patient visit. In the event of an emergency where the attending physician did not have the full medical record for the individual, he could access the data bank through the data carrier.

Such a system could be expanded to embody automatic inprocessing to a hospital or other health care facility. In accordance with this aspect of the subject invention, the individual's medical history would be electroncially transferred between communicating computers of the data bank and hospital. Instead of relying on the individual's memory and accuracy in filling out admittance forms, the patient would simply use his data carrier to access a central data bank programmed to automatically input all necessary information, credit clearances, etc. Substantial time savings and improved treatment could be realized by the quick and accurate flow of information which accompanies the inventive method.

It will be apparent to one skilled in the art, based upon the foregoing explanation, that the scope of the subject invention relates to the establishment of a personal data bank which may be available to authorized persons who satisfy certain entry requirements. For health emergencies, such entry requirements for third parties may be minimal. Where information becomes more sensitive, greater controls can be implemented.

The subject data carrier represents an access key which can be used to implement such a system. The individual controls the type and content of files, as well as limiting access to a certain class of persons. It should therefore be apparent that applications of the inventive system are very broad. It provides an effective means of identification of military personnel, as a replacement for a dog tag. It can be used to control access to certain areas for business or other purposes. For example, certain security conditions, such as computer or data access, can be implemented by scanning the data carrier for authorization for clearance and checking the scan for the required security access code.

In view of the foregoing, it is to be understood that the scope of the present invention is not to be limited by the preferred examples, but to the claims hereafter set forth.

I claim:

1. A method for applying and retaining a data wafer to a living body wherein all phases of installation and detection of the carrier involve noninvasive techniques which are applied with respect to surface tooth structure of the body, said method being comprised of the steps of:

a. selecting a carrier material compatible with the oral environment and adapted for permanent positioning on a surface of the body's tooth structure;
   b. preparing a thin wafer of a thickness less than 10 mils of said carrier material (i) to include a singularly unique identification configuration capable of detection as a unique identification for said body and (ii) to have dimensional properties which enable attachment of the wafer to a single tooth surface while preserving existing comfort and space conditions in the mouth when in place, said identification configuration having information which is capable of being retrived by noninvasive means with respect to tooth structure; and
   c. attaching the thin wafer at a surface of the single tooth without causing damage to tooth enamel or other permanent tooth structure.

2. A method for applying and retaining a permanent data carrier to an individual wherein all phases of installation and detection of the carrier involve passive, noninvasive techniques which are applied with respect to surface tooth structure of the individual, said method being comprised of the steps of:

a. selecting a carrier material compatible with the oral environment and adapted for permanent positioning on a surface of the individual's tooth structure;
   b. preparing a thin wafer of the carrier material with dimensions less than 5 mm×5 mm and a thickness less than 10 mils;
   c. modifying the carrier wafer with a data format representing unique information relating exclusively to the individual; and
   d. permanently attaching the carrier to the surface of the tooth.

3. A method as defined in claim 1, wherein the step of preparing said carrier material comprises the steps of forming a thin chip of flexible material which has individual data positioned on one surface in a detectable form, said chip having a maximum thickness of 9 mils and dimensions less than 200 mils on each side.

4. A method as defined in claim 1 wherein the thin wafer includes deformable material which can be conformed to the approximate surface configuration of the tooth to which it is attached.

5. A method as defined in claim 2 wherein the carrier wafer is attached to the lingual side of a molar tooth.

6. A method as defined in claim 1, wherein the singular unique surface configuration on the carrier includes coded data relevant to the personal identification of the individual.

7. A method as defined in claim 1, wherein the singularly unique surface configuration on the carrier includes coded data relevant to emergency information pertinent to the individual.

8. A method as defined in claim 1, wherein the singularly unique surface configuration on the carrier includes coded data relevant to emergency medical information pertinent to the individual.

9. A method as defined in claim 1, wherein the singularly identification configuration on the carrier comprises encoded data capable of being deciphered by reading means adapted for use within the mouth and communicating with means for deciphering the encoded data.

10. A method as defined in claim 1, wherein the singularly unique surface configuration on the carrier comprises encoded data which can be deciphered by reading means adapted for use within the mouth and which permits visual identification of the carrier data.

11. A method as defined in claim 10, wherein the data includes encoded information adapted for manual entry into computer means for conversion of the encoded data to information in a usable form.

12. A method as defined in claim 10 wherein the data includes encoded information adapted for automated entry into computer means for conversion of the encoded data to information in a usable form.

13. A method as defined in claim 1, further comprising the step of providing additional personal information within a primary data base independent from the individual, and enabling access to the data base by use of the information contained on the carrier.

14. A method as defined in claim 13, wherein the data base contains information relevant to the individual which is capable of being updated as part of a current information source adapted for access by use of data on the carrier.

15. A method as defined in claim 2 wherein the carrier wafer is adapted in size and configuration for application to a child's tooth as part of a method of identification for lost or kidnapped children.

16. A method as defined in claim 2 wherein the carrier wafer is adapted in size and configuration for application to an adult's tooth as part of a method of identification for unconscious or amnesiac persons.

17. A method as defined in claim 2 wherein the carrier wafer is adapted in size and configuration for application to an adult tooth as part of a method of identification of individuals having health deficiencies.

18. A method as defined in claim 1, further comprising the steps of (i) storing a medical history for the individual in a data form which can be retrieved by reference to information on the carrier and (ii) accessing the carrier for the medical history as part of inprocessing in preparation for medical examination.

19. A method as defined in claim 18, wherein the procedure for accessing the individual's medical history is part of an inprocessing sequence for admittance to a health care facility, and further comprises the step of loading the medical history directly into electronic data files of the facility from separate electronic files of the individual wherein access to the individual's files is accomplished automatically be detection of information on the carrier and entry of such information into a communication link between the respective data files in accordance with a control algorhythm.

20. A method as defined in claim 1, wherein the carrier includes information required to gain access to a security condition, and further comprises the steps of (i) scanning the carrier for authorization for clearance with security detection means coupled to access control means for the security condition, (ii) identifying information on the carrier relevant to the security condition and (iii) comparing the information with clearance requirements to reject or approve access of the individual to the security condition.

21. A method as defined in claim 1 further comprising the preliminary steps of:
 exposing enamel rods of the tooth area to which the carrier is to be attached;
 applying a bonding material to the exposed enamel rods as a substrate for the carrier material; and
 bonding the modified carrier material to the substrate while preserving the information in a form adapted for ready detection by passive, noninvasive means.

22. A method as defined in claim 21, wherein the enamel rods are exposed by a process of acid etch in which an oral compatible acid is applied to the surface of the tooth to remove plaque and other superficial material covering the enamel rods.

23. A method as defined in claim 21, wherein the bonding material applied to the enamel rods is also a compatible bonding agent for the selected carrier material.

24. A method as defined in claim 21, further comprising the step of coating the attached carrier with a transparent layer of protective polymer compatible with the bonding material used to attach the carrier to the tooth.

25. A method as defined in claim 1, wherein the selected carrier material comprises a thin plastic film suitable for placement within the oral environment, said film being modified by depositing visible data on one surface of the film as the unique surface configuration in a format which can be readily accessed by third parties without regard to the mental alertness of the individual.

26. A method of identifying a living body having exposed tooth structure wherein all steps of the method involve noninvasive techniques which are applied with respect to surface structure of the tooth, said method comprising the steps of:
 a. selecting a carrier material compatible with the oral environment;
 b. preparing a thin wafer of said carrier material (i) to include a unique identification for the body, and (ii) to have dimensional properties which enable attachment of the wafer to a single tooth surface without substantially affecting comfort conditions at the tooth when in place; and
 c. attaching the thin wafer at a surface of the single tooth without causing damage to tooth enamel or other permanent tooth structure.

* * * * *